US008366935B2

(12) United States Patent
Katz et al.

(10) Patent No.: US 8,366,935 B2
(45) Date of Patent: Feb. 5, 2013

(54) PHYLLANTHUS EXTRACT

(75) Inventors: Aron Katz, Denver, CO (US);
Christopher Molloy, Hertfordshire (GB); Mark Stuart Butler, Brisbane (AU); Brinda Somanadhan, Singapore (SG)

(73) Assignee: Phytrix Inc.

( * ) Notice: Subject to any disclaimer, the term of this patent is extended or adjusted under 35 U.S.C. 154(b) by 361 days.

(21) Appl. No.: 12/642,877

(22) Filed: Dec. 21, 2009

(65) Prior Publication Data

US 2010/0190726 A1 Jul. 29, 2010

Related U.S. Application Data

(63) Continuation of application No. 12/437,169, filed on May 7, 2009, now abandoned.

(60) Provisional application No. 61/051,083, filed on May 7, 2008.

(30) Foreign Application Priority Data

May 7, 2008 (EP) ..................................... 08008623

(51) Int. Cl.
*B01D 15/08* (2006.01)
(52) U.S. Cl. ..................... 210/635; 210/656; 210/198.2; 424/725; 424/775
(58) Field of Classification Search .................. 210/635, 210/656, 659, 198.2, 502.1; 424/725, 775
See application file for complete search history.

(56) References Cited

U.S. PATENT DOCUMENTS

| | | | | |
|---|---|---|---|---|
| 4,879,376 A | * | 11/1989 | Foresta et al. | 536/18.1 |
| 6,586,015 B1 | * | 7/2003 | Gebhardt et al. | 424/725 |
| 6,589,570 B1 | * | 7/2003 | Thyagarajan | 424/725 |
| 7,435,433 B2 | * | 10/2008 | Khanuja et al. | 424/775 |
| 2004/0161477 A1 | * | 8/2004 | Wagner et al. | 424/725 |
| 2008/0280890 A1 | * | 11/2008 | Patil | 514/227.8 |
| 2010/0190726 A1 | * | 7/2010 | Katz et al. | 514/23 |

* cited by examiner

*Primary Examiner* — Ernest G Therkorn
(74) *Attorney, Agent, or Firm* — MDIP LLC

(57) ABSTRACT

A method is described for producing an extract of *Phyllanthus* comprising the steps of: (a) extracting *Phyllanthus* components with a solvent; (b) fractionating the extract obtained in the preceding step on the basis of hydrophobicity; (c) collecting and combining fractions that correspond in hydrophobicity to elute fractions resulting from 10-50% methanol elution steps, wherein the elute fractions are obtained by low pressure vacuum liquid chromatography (VLC) using a C18 reversed-phase lipophilic column and a water/methanol gradient system, wherein the gradient system is based on an initial elution step of loading the column with 100% water, on intermediate elution steps with gradually decreasing water content and on a terminal elution step loading the column with 100% methanol; and (d) optionally drying the extract obtained in step (c). The invention also relates to an extract of *Phyllanthus* obtainable or obtained by the method or a fraction thereof and a *Phyllanthus* extract or fraction thereof comprising repandusinic acid, wherein the repandusinic acid is present at a concentration of at least 42 mg/g.

5 Claims, 3 Drawing Sheets

PHYLLANTHUS EXTRACT

FIELD OF THE INVENTION

The present invention relates to a method for the production of an extract of *Phyllanthus* comprising the steps of: (a) extracting *Phyllanthus* components with a solvent; (b) fractionating the extract obtained in the preceding step on the basis of hydrophobicity; (c) collecting and combining fractions that correspond in hydrophobicity to elute fractions resulting from 10-50% methanol elution steps, wherein said elute fractions are obtained by low pressure vacuum liquid chromatography (VLC) using a C18 reversed-phase lipophilic column and a water/methanol gradient system, wherein the gradient system is based on an initial elution step of loading said column with 100% water, on intermediate elution steps with gradually decreasing water content and on a terminal elution step loading said column with 100% methanol; and (d) optionally drying the extract obtained in step (c). Further, the invention relates to an extract of *Phyllanthus* obtainable or obtained by the latter method or a fraction thereof and a *Phyllanthus* extract or fraction thereof comprising repandusinic acid, wherein the repandusinic acid is present at a concentration of at least 42 mg/g. Also contemplated is a pharmaceutical composition comprising the extract or fraction thereof of the invention, the extract or the fraction thereof of the invention for the prevention and/or treatment of a human immunodeficiency virus (HIV)-associated disease and finally a method to prevent and/or treat the latter.

Several documents are cited throughout the text of this specification. The disclosure content of the documents cited herein (including manufacturer's specifications, instructions, etc.) is herewith incorporated by reference.

BACKGROUND OF THE INVENTION

Human immunodeficiency virus (HIV) is a retrovirus belonging to the primate lentiviruses that can lead upon successful infection to a condition termed acquired immunodeficiency syndrome (AIDS). Said condition is characterized in that the immune system begins to fail and therefore the patient's body becomes increasingly susceptible to secondary and/or recurring infections. The infection with HIV occurs by, e.g., transfer of blood, semen, vaginal fluid and also breast milk. Due to the presence of unbound infectious virus particles in body fluids the rate of infection is high. In particular, sexual intercourse and transmission from infected mothers to their babies as well as feeding with breast milk account for a majority of new HIV cases.

Since becoming a pandemic in the 1980's HIV has received much attention both in the general public as well as in the scientific community. The World Health Organization (WHO) and the Joint United Nations Programme on HIV/AIDS (UNAIDS) have recently estimated that about 25 million people have died due to AIDS since 1981 making it one of the most destructive pandemics in history. This can be linked back to the unique way of cellular infection, manifestation and persistence of the retrovirus in the body which has not yet been found to be successfully treatable.

Presently, treatment of HIV infected patients relies on combination therapies such as, e.g., highly active antiretroviral therapy (HAART), that may be expensive, cause serious drug-related side effects and may give rise to resistant HIV strains after prolonged progression of the therapy. Conventional combination therapies comprise nucleoside-analogue reverse transcriptase inhibitors (NARTIs or NRTIs), non nucleoside-analogue reverse transcriptase inhibitors (NNRTIs) and/or protease inhibitors.

In addition to reverse transcriptase and protease inhibitors, therapeutic drugs for the treatment or prevention of HIV-related diseases have been and continue to be developed which interfere with the process of binding and entry of HIV into its target cells. The process of HI-viral entry into a target cells represents the first step in the viral infection circle. It is characterized by a complex series of events that are initiated through the binding of the viral surface glycoproteins to specific receptor molecules on the cell's outer membrane. This interaction is thought to trigger a conformational change in the viral glycoprotein, which then mediates fusion of the lipid bilayers of the cell and viral membranes and allows the genetic material of the virus to be introduced into the host-cell cytoplasm.

A more detailed view shows that CD4 is the main receptor for HIV which is a 60 kD molecule on the surface of certain immune cells such as, e.g., T lymphocytes, cells of the monocyte/macrophage lineage, or dendritic, antigen-presenting cells (Weiss, R. A. (1993), The retroviridae, 2nd edition (ed. J. A. Levy), pp. 1-108. Plenum Press, New York), and is endogenously involved in T-cell activation (Sweet et al. (1991), Curr. Opin. Biotechnol. 2: 622-633). The virus enters $CD4^+$ cells and after successful amplification and budding of progeny virus particles lyses the infected $CD4^+$ cells. Hence, a hallmark of acquired immunodeficiency syndrome (AIDS) is the depletion of $CD4^+$ cells. The binding of HIV to $CD4^+$ cells involves the formation of a stable complex between CD4 and gp120, the glycoprotein exposed on the envelope of HIV that mediates binding and subsequent entry into the host cell. CD4 has shown to be necessary and sufficient for efficient HIV attachment to target cells. Nevertheless, its presence alone is not sufficient for viral entry and the importance of secondary/fusion receptors could subsequently be established that mediate the fusion of the virus particle and the target cell. This requirement of the presence of a secondary/fusion receptor appears to be so far unique to primate lentiviruses. Several studies identified the CXCR4 and the CCR5 receptor which have been shown to mediate the fusion of virus particles with different tropisms and the respective target cell. The CXCR4 receptor seems to be specific for T-cell tropic HIV strains whereas the CCR5 receptor seems to be specific for M-tropic strains Thus, the gp120/CD4 interaction in connection with the subsequent interaction with the above-identified coreceptors CXCR4 and CCR5 provides a potential target for invention in HIV infections. A number of antibodies and small molecules have been developed as blockers or inhibitors of the gp120/CD4 interaction by binding either gp120 or CD4 (Vermeire et al. (2006), Curr. Med. Chem., 13, 731). Common blockers or inhibitors include but are not limited to antisense molecules, antibodies, antagonists, traps, and their derivatives. However, so far none of these approaches has led to a clinically approved drug.

*Phyllanthus* extracts have been described as antiviral agents in the art. Thus, it has been reported in U.S. Pat. No. 4,937,074 that certain compounds from *Phyllanthus niruri* whole plant extracts may inhibit reverse transcriptase (RT) activity of retroviruses such as HIV. According to Liu et al., Planta Medica 1999, 65, 43-46 certain ellagitannins obtained from *Phyllanthus myrtifolius* and *Phyllanthus urinaria*, including corilagin and geraniin, have an inhibitory effect on Epstein-Barr virus DNA polymerase. It has further been shown by Notka et al., Antiviral Res. 2004, 64(2), 93-102 and Notka et al., Antiviral Res. 2003, 58(2), 175-186 that aqueous ethanolic extracts of *Phyllanthus amarus* Schumach. &

Thonn. (*Euphorbiaceae*) display both in vitro and in vivo anti-HIV activity. The major gallotannin geraniin was shown to be the main active component of the extract. In addition, other active compounds, namely corilagin and sulfated polysaccharides, and inactive compounds, namely ellagic acid, acidic polysaccharides and phyllanthin, were identified. Tanaka et al., Chem. Pharm. Bull. 1996, 44(1), 34-40 have shown that repandusinic acid is a biosynthetic derivative of geraniin. The anti-HIV activity of this compound has been reported by Ogata et al., AIDS Res. Hum. Retroviruses 1992, 8(11), 1937-1944 and Xu et al., Biol. Pharm. Bull. 2000, 23(9), 1072-1076 being an HIV-1-reverse transcriptase inhibitor and HIV-1 protease inhibitor, respectively.

As evidenced by the above details the efforts to identify and develop more efficient drugs and therapies to successfully address the increasing rate of new HIV infections, of progression to AIDS and the increasing death toll linked to the latter are intense and ever increasing in view of the rapidly growing knowledge of HIV and its interaction with the human host. Despite said efforts there is still room for improvement of therapeutic strategies and their technical implementation to successfully prevent or to treat HIV infection.

SUMMARY OF THE INVENTION

The technical problem underlying the present invention was to identify alternative and/or improved means and methods aimed at the prevention and/or treatment of a human-immunodeficiency-virus (HIV)-associated disease.

The solution to this technical problem is achieved by providing the embodiments characterized in the claims.

Accordingly, the present invention relates in a first embodiment to a method for the production of an extract of *Phyllanthus* comprising the steps of:
  a. extracting *Phyllanthus* components with a solvent;
  b. fractionating the extract obtained in the preceding step on the basis of hydrophobicity;
  c. collecting and combining fractions that correspond in hydrophobicity to elute fractions resulting from 10-50% methanol elution steps, wherein said elute fractions are obtained by low pressure vacuum liquid chromatography (VLC) using a C18 reversed-phase lipophilic column and a water/methanol gradient system, wherein the gradient system is based on an initial elution step of loading said column with 100% water, on intermediate elution steps with gradually decreasing water content and on a terminal elution step loading said column with 100% methanol; and
  d. optionally drying the extract obtained in step (c)

BRIEF DESCRIPTION OF THE FIGURES

The following description of the figures and the respective drawings are non-limiting examples that depict various embodiments that exemplify the present invention.

DETAILED DESCRIPTION OF THE INVENTION

Figure 1:
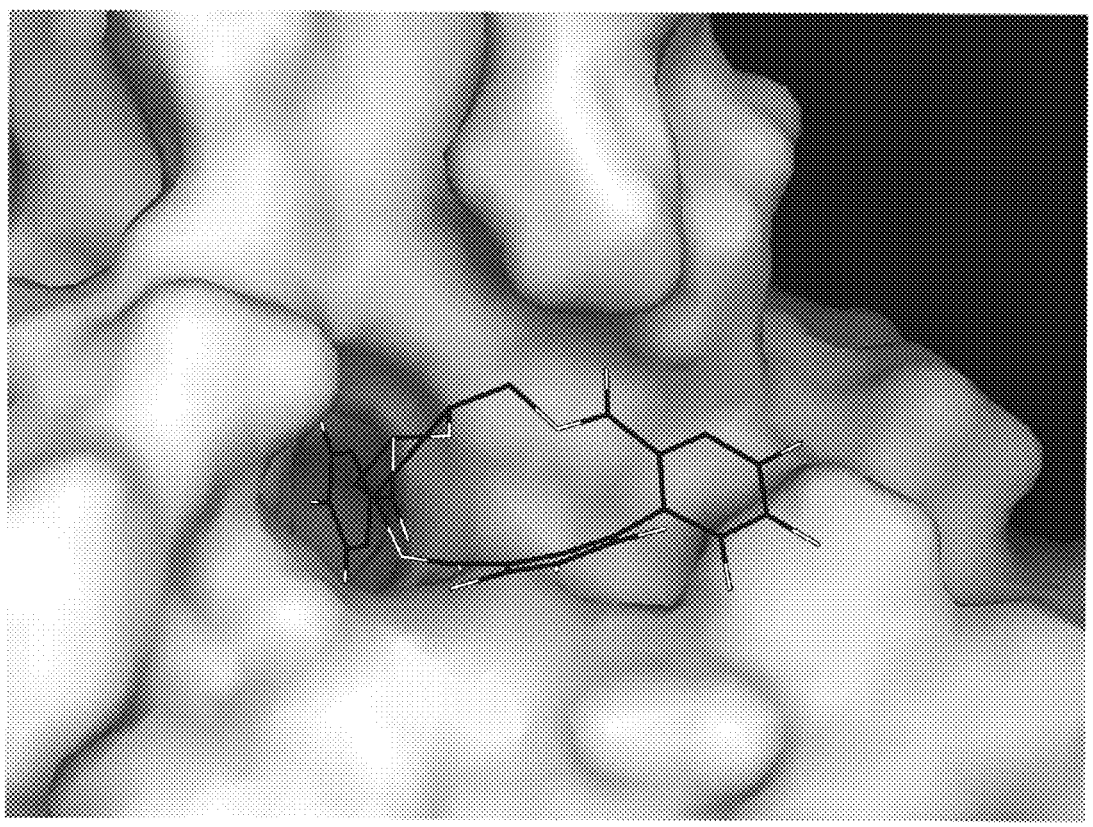
FIG. 1 shows the modeled docking of repandusinic acid to gp120. Other compounds of the gallotannin fraction, i.e. corilagin or geraniin inter alia, are structurally very similar and hence are expected to bind in a similar manner with varying affinities.

"Extracting" as used herein is meant to be a process of solubilising compounds that are contained in the material to be extracted and subsequent release of those compounds from said material. Methods to extract plant material, in particular *Phyllanthus* plants, are well-known in the art and described for example in Liu et al., Planta Medica 1999, 65, 43-46 or; Notka et al., Antiviral Res. 2003, 58(2), 175-186. Extraction procedures may be based on a variety of parameters such as, e.g., weight, size or solubility/polarity, depending on the targeted compounds. Preferably, the extraction is based on solubility. Solubility describes the capability of a substance to dissolve in a solvent and is a function of temperature, pressure and polarity.

The term "*Phyllanthus* components," as used according to the invention, comprises all the components of a whole plant, such as e.g. leaves, bark, blossoms, stalk, seeds, fruit, branches, stems, roots, wood, as well as parts thereof. These *Phyllanthus* components may exhibit the same, similar or non-related ingredients. In the method according to the invention, different *Phyllanthus* components can be used individually or together and different *Phyllanthus* components of different *Phyllanthus* varieties can be used individually or combined together. *Phyllanthus* components can also refer to the whole of *Phyllanthus* components, for example in the form of a whole plant. In the method according to the invention, the *Phyllanthus* components can be used after pre-treatment or without pre-treatment. Pre-treatment comprises, for example, processes such as drying or freeze-drying, for example of, leaves.

The term "fractionating", as used in accordance with the present invention relates to the process of separating a heterogeneous mixture into certain fractions comprising either a single substance or a combination of substances, wherein the composition of said fractions changes according to a gradient. Methods to fractionate plant extracts are well-known in the art and described in, e.g., Seidel in "Natural Products Isolation, Second Edition", ed. Sarker, Latif and Gray, Humana Press, Totowa N.J., 2006, pp 27-46; Romanik et al., J. Biochem. Biophys. Methods 2007, 70 (2), 253-261; Wang and Weller, Trends in Food Science & Technology, 2006, 17(6), 300-312. In general, fractionation may be based on several properties such as, e.g., weight, size, charge, reactivity, or polarity. In accordance with the invention, the fractionation of the method of the present invention is based on hydrophobicity of the substances in the crude *Phyllanthus* extract obtained in the preceding step (a).

The term "hydrophobicity" in accordance with the invention relates to the ability of a substance to be soluble in water and is a function of its polarity. The more hydrophobic a substance is, the inferior is its solubility in water and the better in lipophilic solvents such as, e.g., alcohols with long alkyl chains, i.e. most alcohols except methanol, ethanol and propanol.

In step (c) of the method of the invention fractions are collected according to their hydrophobicity, wherein the fractions correspond in their hydrophobicity to fractions that have been obtained from elute fractions resulting from low pressure Vacuum Liquid Chromatography (VLC) using a C18 reversed-phase lipophilic column and a water/methanol gradient system, wherein the gradient system is based on an initial elution step of loading said column with 100% water, on intermediate elution steps with gradually decreasing water content and on a terminal elution step loading said column with 100% methanol. The skilled person is well-aware of methods to that are suitable in obtaining fractions that correspond in hydrophobicity to said elute fractions. For example, several chromatographic methods are known in the art such as, e.g., reversed-phase HPLC, reversed-phase MPLC, counter current chromatography, super critical fluid chromatography or other chromatography supports such as phenyl, phenylhexyl, amino, cyano, diol, $C_4$, or $C_8$ Silica gel, ion exchange resins (anion and cation), polyamide, XAD, SP207 or HP20 or Sephadex-type such as G-10, G-25 or LH-20. Said methods are well-known in the art and described, e.g., in "Natural Products Isolation, First Edition", ed. Cannell, Totowa N.J., 1998 and "Natural Products Isolation, Second Edition", ed. Sarker, Latif and Gray, Humana Press, Totowa N.J., 2006, that are suitable to generate fractions that can be collected and combined in accordance with the method of the invention. Preferably, the fractionation is performed using the method of low pressure VLC using a C18 reversed-phase lipophilic column and a water/methanol gradient system as described herein-above and in the example section (cf. Example 1).

The optional step of drying the extract obtained in step (c) of the method of the invention can be effected by methods well-known in the art under conditions that do not alter the characteristics, in particular the functional characteristics, of the substances comprised in said extract. Such methods include, e.g., freeze-drying, (vacuum) evaporation or heating.

*Phyllanthus* extracts have previously been described in the art as antiviral agents such as, e.g., against HBV (WO 02/087600) and retroviral infections (EP-B1 1333848), evidencing the capability of the extract to inhibit virus propagation due to inhibitory effects on viral reverse integrase and decreased virus uptake. The present invention, however, is based on the successful identification of the specific agents responsible for the inhibition of viral uptake and, importantly, their functional implication in the latter process. Said implication has been found to be the inhibition of the binding of gp120 to CD4 by binding of the extract to gp120. This finding consequently enabled the inventors to specifically enrich for those specific agents in a crude *Phyllanthus* extract to obtain an extract with improved efficiency and potency in inhibiting the binding of gp120 to CD4 over prior art extracts.

Namely, it has been successfully demonstrated that compounds belonging to the gallotannin fraction bind to a region on the gp120 molecule which is essential in initiating the binding to CD4. In brief, it was found that the gallotannin fraction comprises compounds such as, e.g., repandusinic acid and geraniin, covalently binding to a region around a hydrophobic pocket on gp120 and also binding inside said pocket (cf. Examples 2 and 3; FIG. 1). The importance of said pocket in the coupling event of gp120 to CD4 lies in the fact that the Phe43 residue of the CD4 molecule has been found to enter into said pocket when binding to gp120.

Figure 2:
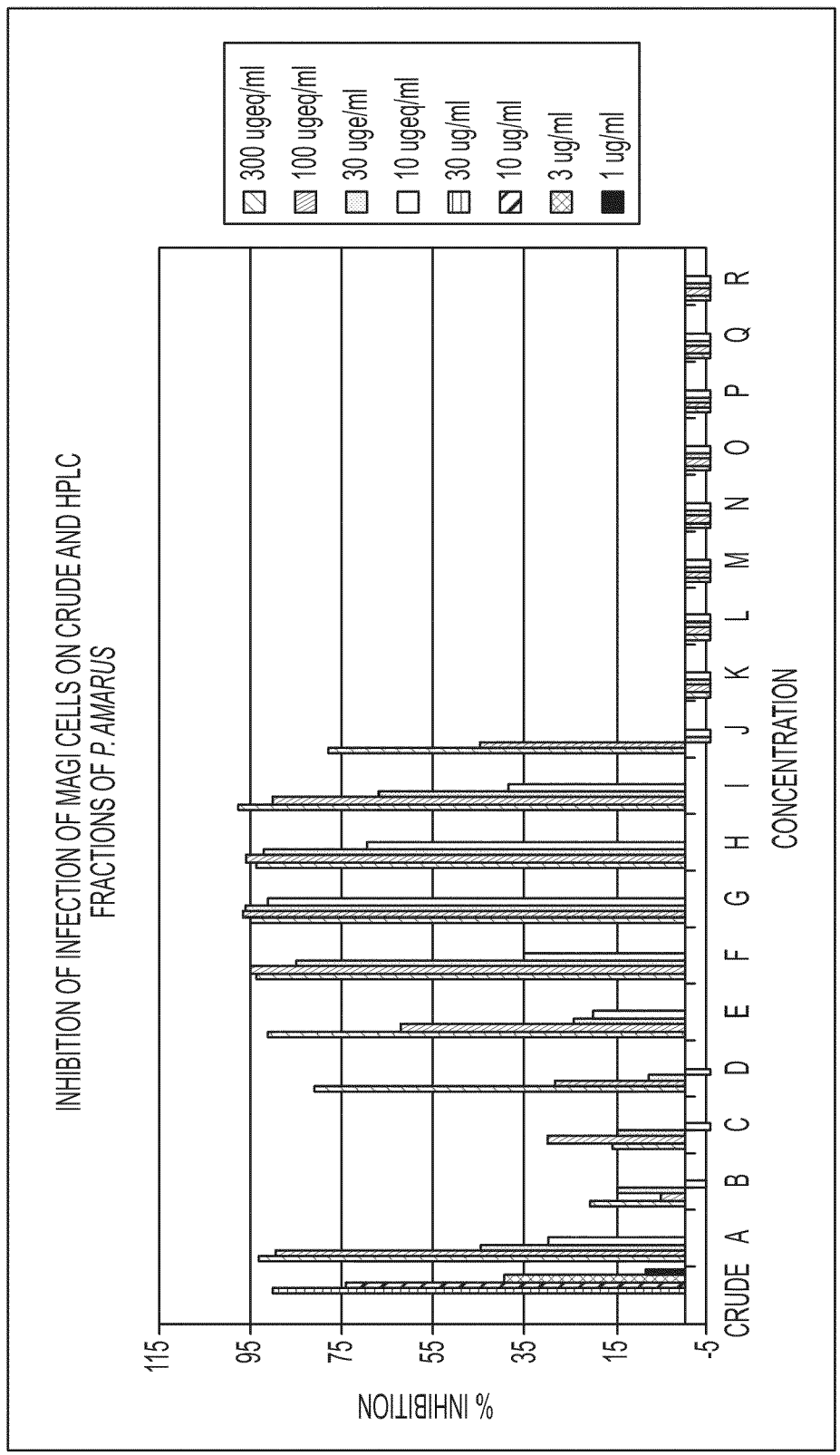
FIG. 2 shows MAGI assay (cf. Example 4) results of crude *Phyllanthus* extract at 30, 10, 3 and 1 µg/ml. HPLC fractions of the crude extract are shown at ~300, 100, 30 and 1 µg eq/ml are depicted, Fractions E to I correspond to the gallotannin fraction that is enriched by the method of the invention and found in the extract of the invention.

Accordingly, once the compounds of the extract are bound to gp120 they are capable of sterically inhibiting the attachment of said Phe43 residue to gp120 which in consequence prevents CD4 from binding to gp120. Inhibition-of-infection assays (cf. Example 4; FIG. 2) underlined the increased potency of specific gallotannin fractions in contrast to crude, i.e. not further fractionated *Phyllanthus* extract which are specifically enriched for in the extract of the invention, viz. repandusinic acid, geraniin and corilagin, that have shown to bind to gp120 in a manner as described herein.

In accordance with the invention the above described finding allows the preparation of an extract that is more effective in inhibiting the binding of gp120 to CD4 and hence viral uptake than the previously known crude extracts. In particular, it is of note that this enriched extract is also superior to other currently developed drugs directed at the inhibition of viral uptake. For instance, some drugs do not prevent the binding of gp120 to CD4 but merely the interaction with one or both of the coreceptors to inhibit fusion with the target cell. Other drugs bind to CD4 and thereby inhibit binding to gp120, however, having the potential drawback of altering the endogenous function of CD4 leading to impairment of the immune system and other adverse side effects. In contrast, the *Phyllanthus* extract of the invention acts by inhibiting the primary step in the infection circle by masking the binding region for CD4 on the gp120 molecule thereby protecting $CD4^+$ cells by spatially separating them from HIV particles. Consequently, this method of action guarantees the effectiveness of the *Phyllanthus* extract independent of the HIV strain and without having a negative effect on the immune system. It is also important to note that the binding area of the extract on the gp120 molecule has been shown to be a very conserved region making the extract highly efficient with regard to treatment of different HIV variants developing throughout the different stages of the infection which are mostly concomitantly present in a patient, and equally important, the risk of developing a resistance to the extract may be diminished.

In a preferred embodiment of the method of the invention, the *Phyllanthus* components are extracted in step (a) with water, an alcohol, a water/alcohol mixture, hexane or $CO_2$.

Methods for extracting plant material with the solvents water, alcohol, water/alcohol mixtures, hexane or $CO_2$ are well known in the art and based upon the solubility of the plant substances to be extracted in the respective solvents. Depending on the solvent chosen obtained extracts can vary in their composition. Preferred is $CO_2$ extraction of *Phyllanthus* components which is a method well known in the art and described, for example, in U.S. Pat. No. 4,554,170 or in Wang and Weller, Trends in Food Science & Technology, 2006, 17(6), 300-312. Equally preferred is extraction with supercritical $CO_2$ which is an extraction method based upon the general $CO_2$ extraction but uses $CO_2$ in a fluid state being at or above both its critical temperature (about 31.1° C.) and pressure (about 73 atm). This has the effect of $CO_2$ being in a gaseous state but having a density like liquid $CO_2$. Furthermore, by modulating the density of the medium it can be selective for the range of compounds to be extracted. Advantages are the relatively low temperature at which the extraction process can be conducted with the consequence of less damage to the compounds to be extracted compared to extraction methods using, e.g., water.

Also in accordance with the invention preferably a water/alcohol mixture can be used for extracting *Phyllanthus* components, wherein preferably the alcohol is ethanol.

More specifically, in a further preferred embodiment of the method of the invention, the *Phyllanthus* components are extracted in step (a) with an ethanol/water mixture of 5-85% m/m to which a heavy-metal chelator is added at a final concentration of 0.001-3% m/m.

In accordance with the invention "% m/m" is meant to be % mass/mass and can be calculated by the formula g solute/g solution×100. The person skilled in the art is familiar with this method to determine quantities of substances to be used accordingly in the method of the present invention.

In a further preferred embodiment of the method of the invention, the method comprises a further step (aa) after step (a) and prior to step (b): (aa) contacting and concentrating the extract obtained in step (a) with (i) Indian Sterculia gum at a final concentration of 0.5-5.0% m/m relative to the sum of the extractive substances or (ii) one or more polymers and impendable and/or soluble substance(s).

A method to obtain a crude extract as in step (a) of the invention has been described in EP-B1 1326624 which is herewith expressly incorporated in its entirety by reference. Briefly, extraction of the *Phyllanthus* components with an ethanol/water mixture to which a heavy-metal chelator is added provides the advantage in large-scale extractions of *Phyllanthus* components to avoid the formation of non-soluble macromolecular precipitates of extract compounds such as, e.g., ellagitannins, bound to heavy-metals. The further step (aa) comprising the addition of (i) Indian Sterculia gum or (ii) one or more polymers and impendable and/or soluble substance(s) has the advantage of avoiding sedimentations and floatations of various components of the extract when removing the solvent agent. Further, the choice of a solving agent mixture of average polarity delays extract thickening due to evaporation of a solvent. For this reason, preferably an ethanol mixture of 5-85% m/m, more preferred 35-45% m/m is chosen. Due to the above-described modifications to the extraction method it is possible to obtain a crude extract with minimal loss of inter alia gallotannins during extraction.

In another preferred embodiment of the method of the invention, the *Phyllanthus* components are *Phyllanthus amarus* components.

The plant genus *Phyllanthus* belongs to the sub-family of the *Phyllanthoideae* which belongs to the family of the *Euphorbiaceae*. In total, the genus *Phyllanthus* comprises about 700 known varieties which come from tropical and subtropical areas in Australia, China, the Philippines, Thailand, Indonesia, Burma, India, East and West Africa and North America, Mexico, Cuba, the Caribbean and Venezuela. Only rarely are representative of this genus found in the Northern moderate zones. Preferably, *Phyllanthus amarus* components are used in the method of the invention as they comprise a particularly high proportion of the compounds shown to be active in inhibiting the binding of gp120 to CD4. Even more preferred are *Phyllanthus amarus* components of the *Phyllanthus amarus* variant *Schumach. & Thonn.*

The invention also relates to an extract of *Phyllanthus* obtainable or obtained by the method of the invention or a fraction thereof.

As outlined above, the method to obtain a *Phyllanthus* extract has been developed to obtain an extract that is enriched for the gallotannin fraction and specifically geraniin and repandusinic acid.

Figure 3:
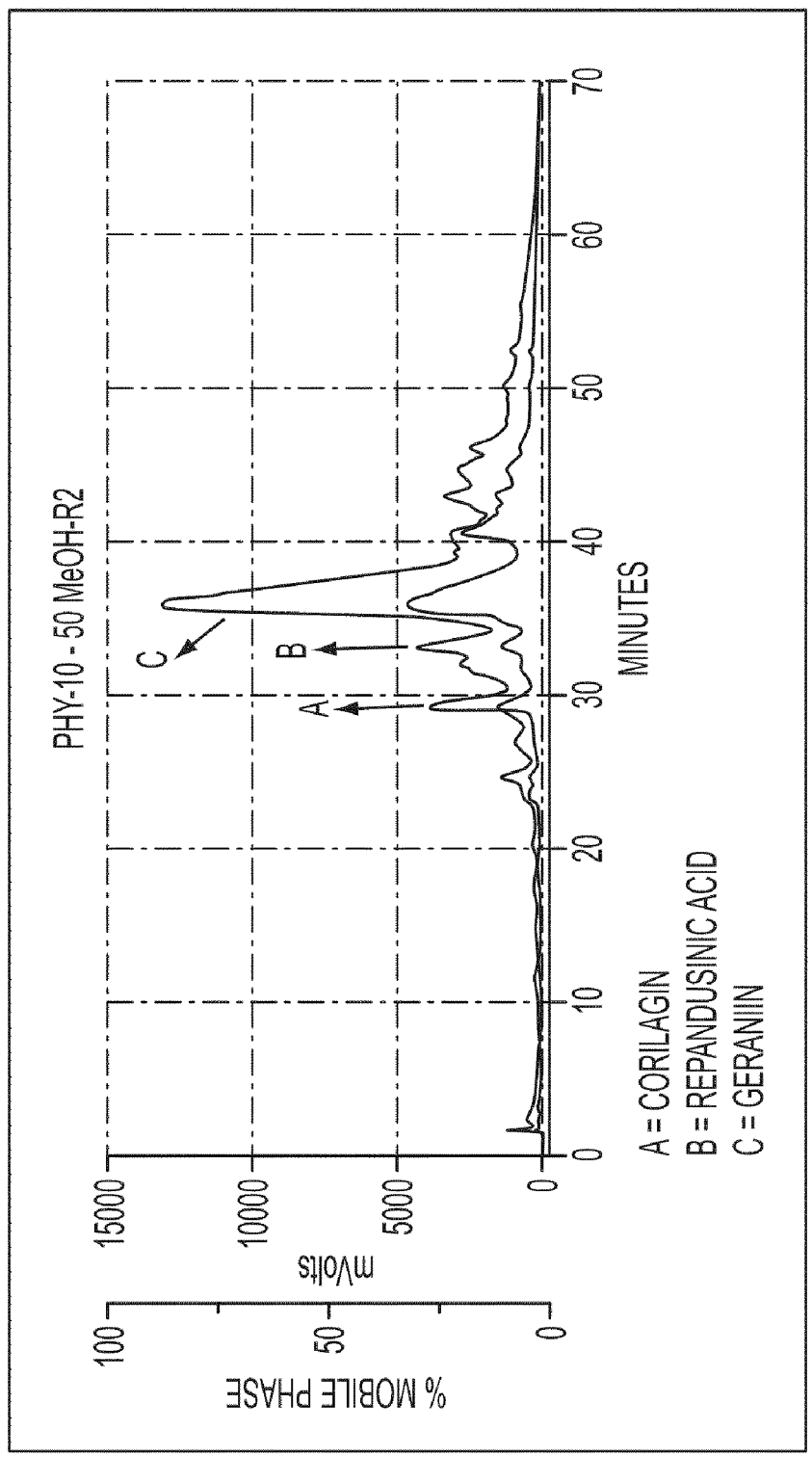
FIG. 3 shows a HPLC chromatogram of the gallotannin fraction in the extract of the invention.

The term "fraction thereof" relates to a fraction of the extract that preferably exhibits the same or improved characteristics as regards the binding to gp120 and thereby inhibiting the binding to CD4. More preferred, said fraction comprises the gallotannin fraction and most preferred one or more of the compounds selected from the group of repandusinic acid, geraniin, corilagin and brevifolin carboxylic acid. The skilled person is in the position to obtain and determine the activity of a corresponding fraction, e.g., by comparing the activity of the fraction of the extract with the activity of the latter extract in a virus-uptake assay. For example, the HPLC spectrum of the gallotannin fraction of an extract in accordance with the invention is depicted in FIG. 3.

Accordingly, in a more preferred embodiment of the extract or fraction thereof of the invention, the extract comprises or the fraction thereof is a gallotannin fraction.

Gallotannins are naturally occurring phenolic compounds that contain a glucose core that is esterified with gallic acid or a derivative of gallic acid. Examples of gallotannins are found, e.g., in Okuda, Phytochemistry 2005, 66(17), 2012-2031; Niemetz and Gross, Phytochemistry 2005, 66(17), 2001-2011 or He at al., Food Chemistry 2006, 95, 250-254.

In a more preferred embodiment of the extract or fraction thereof of the invention, the gallotannin fraction comprises repandusinic acid.

Repandusinic acid has the following chemical structure:

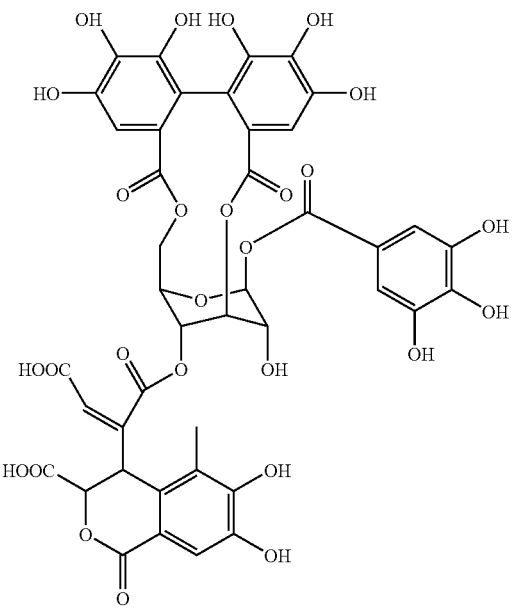 [SMILES: Cc1c(O)c(O)cc2c1C(/C(=C/C(=O)O)C(=O)OC1C3COC(=O)c4cc(O)c(O)c(O)c4-c4c(cc(O)c(O)c4O)C(=O)OC1C(O)C(OC(=O)c1cc(O)c(O)c(O)c1)O3)C(C(=O)O)OC2=O]

In an even more preferred embodiment of the extract or fraction thereof of the invention, the gallotannin fraction further comprises repandusinic acid and one or more compounds selected from the group of geraniin, corilagin and brevifolin carboxylic acid.

The chemical structure of geraniin is as follows:

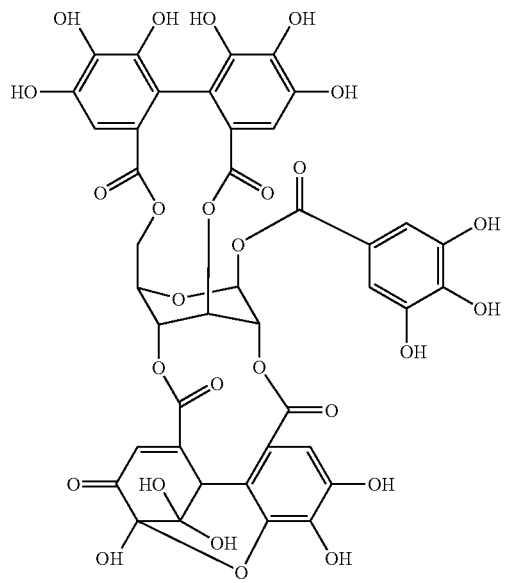 [SMILES: O=C1OC2C3COC(=O)c4cc(O)c(O)c(O)c4-c4c(cc(O)c(O)c4O)C(=O)OC2C(OC(=O)c2cc(O)c(O)c4c2C2C1=CC(=O)C(O)(O4)C2(O)O)C(OC(=O)c1cc(O)c(O)c(O)c1)O3]

The chemical structure of corilagin is as follows:

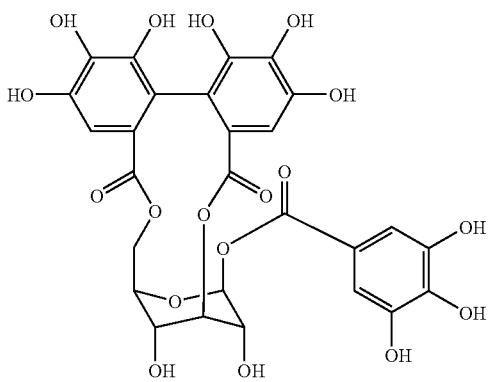 [SMILES: O=C(OC1OC2COC(=O)c3cc(O)c(O)c(O)c3-c3c(cc(O)c(O)c3O)C(=O)OC(C2O)C1O)c1cc(O)c(O)c(O)c1]

Also, the invention relates to a *Phyllanthus* extract or fraction thereof comprising repandusinic acid, wherein the repandusinic acid is present at a concentration of at least 42 mg/g.

An extract having the above-recited concentration of repandusinic acid has shown to be particularly effective in binding to gp120 and inhibiting the binding of the latter glycoprotein to CD4. The extract may be, e.g., obtained by the method of the invention or any other method that is suitable to generate an extract with said specific concentration of repandusinic acid. Preferably the extract has a concentration of at least 42 mg/g such as 50 mg/g, more preferred at least 60 mg/g and most preferred at least 100 mg/g. The extract further comprises compounds such as, e.g., phyllanthin which are characteristic of a *Phyllanthus* extract according to the invention or obtainable or obtained by the method of the invention.

In a preferred embodiment of the extract or fraction thereof of the invention, the extract further comprises one or more compounds selected form the group of geraniin, corilagin and brevifolin carboxylic acid, wherein geraniin is present at a concentration of at least 250 mg/g, corilagin is present at a concentration of at least 37 mg/g or brevifolin carboxylic acid at a concentration of at least 1 µg/g.

Further, the extract or the fraction thereof of the invention comprises further compounds at specific concentrations. Preferably, geraniin, corilagin and brevifolin carboxylic acid are present alone or in any combination at a concentration of at least 1 µg/g such as 10 µg/g, 100 µg/g, more preferred at least 0.25 mg/g and most preferred at least 1 mg/g.

The invention further relates to a pharmaceutical composition comprising the extract or fraction thereof of the invention.

In accordance with the present invention, the term "pharmaceutical composition" relates to a composition for administration to a patient, preferably a human patient. The pharmaceutical compositions described herein can be administered to the subject at a suitable dose. Administration of the compositions may be effected by different ways, e.g., by intravenous, intraperitoneal, subcutaneous, as well as transdermal administration.

The pharmaceutical composition may, accordingly, be administered orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition described herein may comprise further agents depending on the intended use of the pharmaceutical composition.

Pharmaceutically acceptable excipients that may be used in the formulation of the pharmaceutical compositions may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintegrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins. Other suitable pharmaceutically acceptable excipients are described in Remington's Pharmaceutical Sciences, 15th Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the extract of the invention that may be combined with excipients to formulate a single dosage form or separate dosage forms will vary upon the host treated and the particular mode of administration.

The pharmaceutical compositions of the invention can be produced in a manner known per se to the skilled person as described, for example, in *Remington's Pharmaceutical Sciences,* 15th Ed., Mack Publishing Co., New Jersey (1991).

For the purpose of the present invention, a therapeutically effective dosage of the extract of the pharmaceutical composition of the invention will generally be from about 100 to 2000 mg/day, preferably from about 500 to about 1500 mg/day, and most preferably from about 750 to about 1000 mg/day, which may be administered in one or multiple doses. In a most preferred administration scheme of the pharmaceutical composition, the administration of about 500 to 750 mg/day in one or more doses a day is envisaged.

It will be appreciated, however, that specific dose level of the pharmaceutical composition for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician.

The above applies mutatis mutandis for other embodiments described herein.

The invention also relates to the extract of the invention or a fraction thereof for the prevention and/or treatment of a human immunodeficiency virus (HIV)-associated disease.

As used herein, the term "HIV-associated disease" refers in particular to an HIV infection. The term "HIV infection" generally encompasses infection of a host, particularly a human host, by the human immunodeficiency virus (HIV) family of retroviruses including, but not limited to, HIV I, HIV II, HIV III (also known as HTLV-II, LAV-1, LAV-2), and the like. "HIV" can be used herein to refer to any strains, forms, subtypes, classes and variations in the HIV family. Thus, "treatment" of a HIV infection will encompass the treatment of a person who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as an HIV carrier on the basis that the person is anti-HIV antibody positive, or is HIV-positive, or has symptoms of AIDS. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4 positive T cells), and AIDS (which is defined by more serious AIDS-defining illnesses and/or a decline in the circulating CD4 cell count to below a level that is compatible with effective immune function). In addition, "treatment and/or prevention of a HIV-associated disease" will also encompass treating suspected infection by HIV after suspected past exposure to HIV by e.g., contact with HIV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "preventing" also encompasses treating a person who has not been diagnosed as having a HIV infection but is believed to be at risk of infection by HIV.

The usefulness and superiority over prior art strategies to prevent gp120 to CD4 binding has been described and discussed hereinabove. The skilled person, most likely a medical practitioner, is well-aware of the pathology of HIV and hence is in the position to devise a therapy according to general principles known in the art and described, for example, herein above.

Also, the invention relates to a method for preventing and/or treating a HIV-associated disease comprising administering an effective amount of the pharmaceutical composition or the extract of the invention to a subject in need thereof.

In a preferred embodiment of the extract for preventing and/or treating or the method of preventing and/or treating a HIV-associated disease, said disease is a HIV-1- and/or HIV-2-associated disease.

In a more preferred embodiment of the extract for preventing and/or treating or the method of preventing and/or treating a HIV-associated disease, the HIV-associated disease is AIDS.

It is submitted that the skilled person is well-aware of the pathology of AIDS including initiation, progression and clinical outcomes. Accordingly, the impact of a drug that inhibits new infection of the $CD4^+$ cells will lead to a recuperation of said cell population and hence restore the patient's immune system. This has a beneficial effect also on the fight against secondary infections like, e.g., recurring viral infections and bacterial infections, that characterize the medical condition AIDS and are mostly responsible for the death of AIDS patients.

The invention now will be exemplified in the following non-limiting examples.

EXAMPLES

Example 1

Fractionation of Crude *Phyllanthus amarus* Extract

The aqueous EtOH extract (100 g) was dissolved in $H_2O$ (200 ml) and added to the top of $C_{18}$ Silica gel column (17×10 cm) and fractionated by low pressure vacuum liquid chromatography (VLC). Elution was initiated with $H_2O$ (3 L), followed by stepwise elution (2 L each) with 10%, 20%, 30%, 40%, 50%, 75% and 100% MeOH in $H_2O$. The bioactivity was located in the 10% to 50% MeOH in $H_2O$ fractions. These fractions were combined and concentrated in a rotary evaporator at 35 degrees and this represents the gallotannin fraction. This material was further fractionated using the preparative C-18 HPLC (X-terra @prepRP18, 19×30 mm, 5 µM, flow rate 12 ml/min, UV detection 210 nm and 254 nm) using the eluent water-ACN (each with 0.1% HCOOH) gradient system (1:0 to 7:3) for 60 minutes, to get the compounds geraniin, repandusinic acid, corilagin and brevifolin carboxylic acid.

Example 2

Determination of gp120 Binding Constants Using Micro-Equilibrium Dialysis (mED)

Analyses were conducted using Harvard Apparatus DispoEquilibrium Dializers with 10 kDa MWCO loaded with 25 µl of 6 mg/ml of gp120 (25 µM) in PBS pH 7.2 loaded in each apparatus. Each affinity event was prescreened at 10 analyte concentrations from 0.001 to 2.5 mmol in PBS pH 7.2 for each compound screened. If needed, experiments were repeated within a smaller concentration range (i.e., 10 trials from 0.01 to 0.10 mmol). A total volume of either 50 µl was used in each analysis. Analytes were loaded in the opposite side of the membrane and equilibrium was obtained after incubation of 12 hrs at 23° C. The association constants were determined by non-linear regression analysis. Concentrations of compounds analysed were determined by HPLC analysis by comparison against an internal control (diethyl-7-dimethylaminocoumarineacetamide). HPLC controls were run with an equimolar amount of control and analyte. The relative concentrations of each analyte were determined at both sides of the membrane. In all cases the concentration of the control remained equivalent on both sides of the membrane. Each data point was recollected after regeneration of the dialysis setup by exposing the non-protein containing face of the membrane to 5 ml of PBS pH 7.2 twice for 4 to 10 hrs at 23° C. Each data point remained reproducible within five repetitions, and an average and deviation of this data is presented in Table 1.

TABLE 1

Binding affinities of *Phyllanthus* components to gp120

| Name | mg | $K_D$ gp120 in µM |
|---|---|---|
| Repandusinic acid | 1.0 | 0.022 ± 0.008 |
| Corilagin | 0.5 | 0.12 ± 0.06 |
| Geraniin | 0.7 | 0.076 ± 0.015 |
| Gallic acid | 4.7 | ≧100 |
| Phyllanthin | 1.0 | 2.8 ± 0.7 |
| Phyllanthusiin E | 0.7 | 22.1 ± 1.2 |
| Phyllanthusiin E analog | 0.3 | 12.6 ± 2.1 |

The binding affinity ($K_D$) to gp120 of the aforementioned components can be used to prioritize, or rank, the efficacy of these components and to assess relative binding affinities, and therefore potential selectivity of binding, with competing proteins such as serum albumin. The data in Table 1 demonstrate the significant differences in binding affinity toward gp120 across a range of extract component compounds and furthermore demonstrate the discovery of the particular relevance of the components repandusinic acid (22 nM), geraniin (76 nM) and corilagin (120 nM) when compared with components such as phyllanthin (28000 nM). $K_D$ data against bovine serum albumin—which has a wide range of potential binding sites and is used to identify non-specific binding events—indicate that the active components show selectivity toward gp120 (data not shown).

Example 3

Binding Site of Corilagin, Repandusinic Acid and Geraniin

It has been reported that there are at least two binding areas on gp120 that are bound by known inhibitors of gp120-CD4 binding. One site is bound by inhibitors that prevent conformational changes in gp120 protein upon gp120-CD4 binding (Si et al., Proceedings of the National Academy of Sciences, 101(14):5036 (2004)). It is suggested that the important residues are 112, 113, 382, 426, 125, 429, 433 and 457 (Madani et al., J. Virol., 78:3742-3752 (2004)). Other compounds have been identified that prevent the binding of gp120 to CD4 via a specific and competitive mechanism. It was shown that the essential residues are 368, 370, 371, 427, 457 and 375 (Guo et al., J. Virol., 77(19):10528-10536 (2003)). The residues corresponding to the latter site (in the following termed site I) are located into a large cavity, which is penetrated by the phenyl residue Phe43 of CD4 and hence is responsible for gp120-CD4 interaction. Interestingly, it has been found that corilagin, geraniin and repandusinic acid all bind at site I. It could be shown by computational modeling (QUANTUM software) that the compounds all lay in the same relatively small hydrophobic pocket at site I. More specifically, it could be shown that a single phenyl ring with several OH-groups enters the hydrophobic pocket while the remaining part of the compounds occupies the large cavity at site I as shown in FIG. 1. Accordingly, it could be shown that especially the compounds of the gallotannin fraction which quantitatively make up most of said fraction specifically bind into the hydrophobic pocket and hence directly inhibit the binding of gp120 to CD4.

Example 4

MAGI-Assay to Determine Activity of Crude *Phyllanthus* Extract and *Phyllanthus* Extract Fractions Crude *Phyllanthus amarus* Extract Powdered crude *Phyllanthus amarus* extract was reconstituted (A) with phosphate-buffered saline (PBS) to give a final concentration of 1 mg/ml or (B) the extract was first reconstituted in dimethylsulfoxide (DMSO) (Sigma-Aldrich, Deisenhofen, Germany) and diluted in PBS to give a final concentration of 1 mg/ml and 4% DMSO.

HIV Virus Strain $HIV_{NL4-3}$ stock was generated by infection of $5 \times 10^6$ PM1 cells (in 500 µl medium) with 500 µl of the virus strain. Cells were cultured in a volume of 20 ml for 5-7 days and supernatant was cleared of cell debris by low speed centrifugation. An equal volume of fetal calf serum (FCS) was added and 1 ml samples were stored at −80° C.

Infection Of Multinuclear Activation Of Galactosidase Indicator (MAGI) Cells

The MAGI reporter system was developed to generate an easy-to-use and efficient method for quantitative analyses of HIV infectivity on a cellular level (Kimpton and Emerman, 1992). In brief, $3 \times 10^4$ MAGI cells per well were plated in 48-well culture plates and grown overnight. The next day 90 µl of HIV stock was mixed with 10 µl of inhibitor dilutions (final dilutions from 10 µg/ml to 0.05 µg/ml) or PBS. The medium in the culture plates was replaced by the 100 µl HIV stock inhibitor mix and the cells were cultured for in a humidified atmosphere. 2 hours post infection 200 µl of fresh medium with the corresponding *Ph. amarus* dilution was added to each well. Two days after infection, infected cells were detected by 5-bromo-4-chloro-3-indoyl-β-D-galactopyranoside (X-gal) staining of cells expressing an endogenous β-galactosidase as a consequence of HIV infection. Cells were fixed with 0.2% glutaraldehyde and 1% formaldehyde in PBS for 5 min. Fixed cells were washed with PBS twice and overlaid with the staining solution (4 mM K-ferricyanide, 4 mM K-ferrocyanide, 2 mM $MgCl_2$ and 0.4 mg/ml X-gal) for 30 min at 37° C. The number of blue cells was determined by microscopic observation. As is evident from the diagram of FIG. 2 the crude extract was capable of inhibiting viral infection in a dose-dependant manner. The data also demonstrate that the chromatographically separated fractions of the same crude extract—dosed at concentrations equivalent to their concentration within the said crude extract (µg/equivalents, or µgeq)—showed differing activities. This indicates that the activity is directly associated with compounds within a certain range of physicochemical characteristics separable by chromatography (for example, hydrophobicity). The inhibition of viral infection of the crude extract could be mimicked by the gallotannin fractions but not by any of the lignin containing fractions. This finding led to the understanding that anti-HIV properties of the extract may be improved by enrichment of these specific components as opposed to extract standardisation by the presence of certain concentrations of lignins as had been previously performed. By enriching the concentration of the active components and removing inactive components as described in this invention, the efficacy of the new mixture can be improved over and above that seen with the mixture of both active and inactive components within the crude extract.

All references cited herein are herein incorporated by reference in entirety.

We claim:

1. A method for the production of an extract of *Phyllanthus* comprising the steps of:
   (a) extracting *Phyllanthus* components with a solvent;
   (b) fractionating the extract obtained in the preceding step on the basis of hydrophobicity;
   (c) collecting and combining fractions that correspond in hydrophobicity to elute fractions resulting from 10-50% methanol elution steps, wherein said elute fractions are obtained by low pressure vacuum liquid chromatography (VLC) using a C18 reversed-phase lipophilic column and a water/methanol gradient system, wherein the gradient system is based on an initial elution step of loading said column with 100% water, on intermediate elution steps with gradually decreasing water content and on a terminal elution step loading said column with 100% methanol; and
   (d) optionally drying the extract obtained in step (c).

2. The method of claim 1, wherein the *Phyllanthus* components are extracted in step (a) with water, an alcohol, a water/alcohol mixture, hexane or $CO_2$.

3. The method of claim 1 or 2, wherein the *Phyllanthus* components are extracted in step (a) with an ethanol/water mixture of 5-85% m/m to which a heavy-metal chelator is added at a final concentration of 0.001-3% m/m.

4. The method of claim 1, wherein the method comprises a further step (aa) after step (a) and prior to step (b):
   (aa) contacting and concentrating the extract obtained in step (a) with
      (i) Indian Sterculia gum at a final concentration of 0.5-5.0% m/m relative to the sum of the extractive substances or
      (ii) one or more polymers and impendable and/or soluble substance(s).

5. The method of claim 1, wherein the *Phyllanthus* components are *Phyllanthus amarus* components.

* * * * *